US006812016B2

(12) United States Patent
Moeckel et al.

(10) Patent No.: US 6,812,016 B2
(45) Date of Patent: Nov. 2, 2004

(54) NUCLEOTIDE SEQUENCES WHICH CODE FOR THE METY GENE

(75) Inventors: Bettina Moeckel, Duesseldorf (DE); Walter Pfefferle, Halle (DE); Klaus Huthmacher, Gelnhausen (DE); Christian Rueckert, Guetersloh (DE); Joern Kalinowski, Bielefeld (DE); Alfred Puehler, Bielefeld (DE); Michael Binder, Steinhagen (DE); Dieter Greissinger, Niddatal (DE); Georg Thierbach, Bielefeld (DE)

(73) Assignee: Degussa AG, Duesseldorf (DE)

( * ) Notice: Subject to any disclaimer, the term of this patent is extended or adjusted under 35 U.S.C. 154(b) by 109 days.

(21) Appl. No.: 09/919,932

(22) Filed: Aug. 2, 2001

(65) Prior Publication Data

US 2002/0110878 A1 Aug. 15, 2002

Related U.S. Application Data

(60) Provisional application No. 60/294,252, filed on May 31, 2001.

(30) Foreign Application Priority Data

Sep. 2, 2000 (DE) .......................................... 100 43 334
Feb. 28, 2001 (DE) .......................................... 101 09 690

(51) Int. Cl.[7] .............................. C12N 9/14; C12N 1/20
(52) U.S. Cl. ............... 435/195; 435/320.1; 435/252.33; 435/183; 435/106; 435/6; 536/23.1; 536/23.2; 536/23.7
(58) Field of Search ................................. 435/195, 193, 435/106, 6, 183, 320.1, 252.32, 252.3; 536/23.1, 232, 23.7

(56) References Cited

U.S. PATENT DOCUMENTS

| 3,729,381 A | 4/1973 | Nakayama et al. | ......... 435/113 |
|---|---|---|---|
| 2003/0049804 A1 | 3/2003 | Pompejus et al. | .......... 435/115 |

FOREIGN PATENT DOCUMENTS

| DE | 196 44 567 | 4/1998 |
|---|---|---|
| EP | 0 219 027 | 4/1987 |
| EP | 0 387 527 | 9/1990 |
| EP | 1 108 790 | 6/2001 |
| WO | WO 93/17112 | 9/1993 |
| WO | WO 01/00802 | 1/2001 |
| WO | WO 01/00843 | 1/2001 |
| WO | WO 01/00845 | 1/2001 |
| WO | WO 01/00847 | 1/2001 |

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492–495.*
S. D. Park, et al., Database EMBL Online. Accession No. AF052652, XP002185275, 2 pages, "Isolation and Analysis of metA, A Methionine Biosynthetic Gene Encoding Homoserine Acetyltransferase in Corynebacterium Glutamicum", Mar. 20, 1998.
E.S. Drazek, et al., Database EMBL Online. Accession No. AF109162, XP002185276, 3 pages, "Corynebacterium Diphteriae Genes Required for Acquisition of Iron from Haemin and Haemoglobin are Homologous to ABC Haemin Transporters", Jun. 9, 1999.
Shuzo Yamagata, Biochimie, vol. 71, pp. 1125–1143, "Roles of O–Acetyl–L–Homoserine Sulfhydrylases in Micro–Organisms", 1989.
Derwent Publications Ltd., KR 9 208 381, Sep. 26, 1992.
Derwent Publications Ltd., WO 01/00843, Jan. 4, 2001.
B. J. Hwang, et al., Database EMBL Online, Accession No. AF220150, XP002185277, 2 pages, "metZ of Corynebacterium Glutamicum", Jan. 17, 2001.
Reinhard Krämer, Journal of Biotechnology, vol. 45, No. 1, pp. 1–21, "Genetic and Physiological Approaches for the Production of Amino Acids", 1996.
Bernhard J. Eikmanns, et al., Antonie Van Leeuwenhoek, vol. 64, No. 2, pp. 145–163, "Molecular Aspects of Lysine, Threonine, and Isoleucine Biosynthesis in Corynebacterium Glutamicum", 1993.

* cited by examiner

Primary Examiner—Richard Hutson
(74) Attorney, Agent, or Firm—Oblon, Spivak, McClelland, Maier & Neustadt, P.C.

(57) ABSTRACT

The present invention relates to isolated polynucleotides which encode proteins with O-acetylhomoserine sulfhydrylase, vectors and cells containing the polynucleotides as well as methods of preparing L-amino acids.

11 Claims, 2 Drawing Sheets

Figure 1: Plasmid pCREmetY
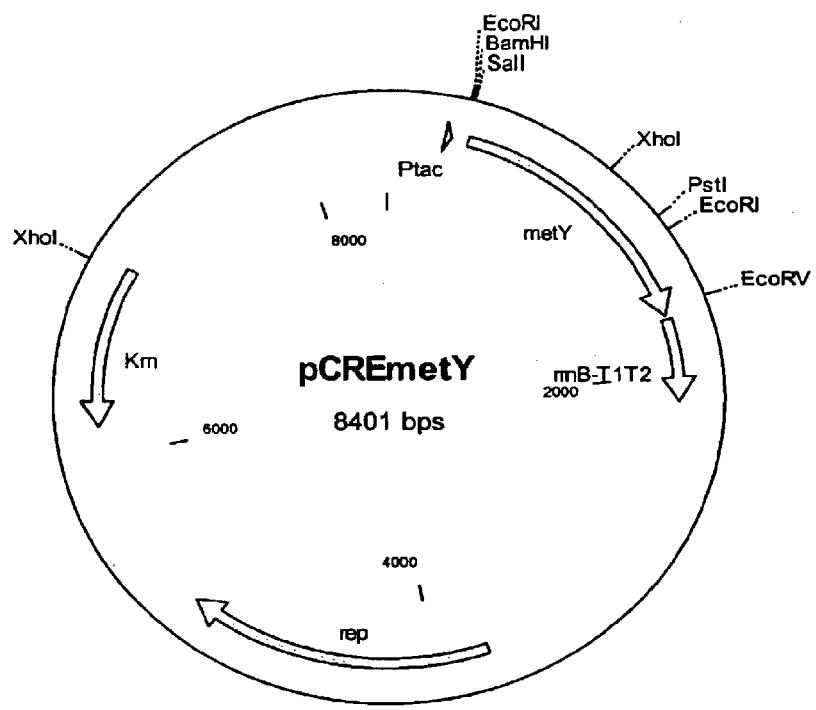

Figure 2: Plasmid pCREmetAY
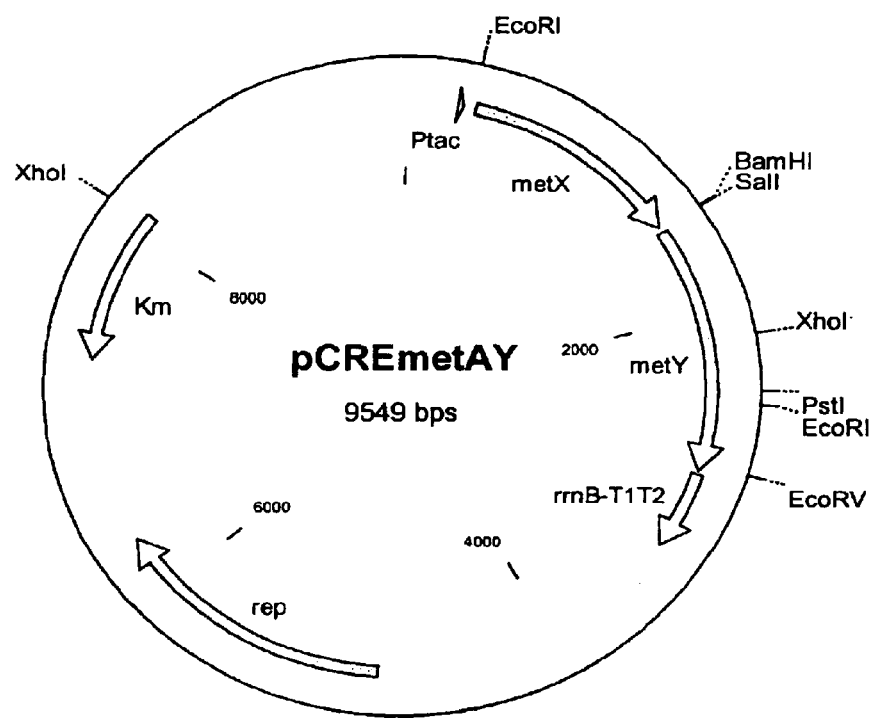

NUCLEOTIDE SEQUENCES WHICH CODE FOR THE METY GENE

BACKGROUND OF THE INVENTION

1. Field of the Invention

The invention provides nucleotide sequences from coryneform bacteria which code for the metY gene and a process for the fermentative preparation of amino acids, in particular L-lysine and L-methionine, using bacteria in which at least the metY gene is enhanced.

2. Description of the Related Art

L-Amino acids, in particular L-lysine and L-methionine, are used in human medicine and in the pharmaceuticals of industry, in the foodstuffs industry and very particularly in animal nutrition.

It is known that amino acids are prepared by fermentation from strains of coryneform bacteria, in particular *Corynebacterium glutamicum*. Because of their great importance, work is constantly being undertaken to improve the preparation process. Improvements to the process can relate to fermentation measures stirring and supply of oxygen, or to the composition of the nutrient media, such as the sugar concentration during the fermentation, or to working up of the product by, for example, ion exchange chormatography, of to the intrinsic output properties of the microorganism itself.

Methods of mutagenesis, selection and mutant selection are used to improve the output properties of these microorganisms. Strains which are resistant to antimetabolites or are auxotrophic for metabolites of regulatory importance and produce amino acids are obtained in this manner.

Recombinant DNA techniques have also been employed for some years for improving the *Corynebacterium* strains which produce L-amino acid, by amplifying individual amino acid biosynthesis genes and investigating their effect on amino acid production.

SUMMARY OF THE INVENTION

An object of the present invention is to provide new measures for improved fermentative preparation of amino acids, in particular L-lysine and L-methionine.

Where L-amino acids or amino acids are mentioned in the following, this means one or more amino acids, including their salts, chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine.

When L-lysine or lysine are mentioned in the following, not only the bases but also the salts, such as lysine monohydrochloride or lysine sulfate, are intended.

When L-methionine or methionine are mentioned in the following, the salts, such as e.g. methionine hydrochloride or methionine sulfate, are intended.

The invention provides an isolated polynucleotide from coryneform bacteria, comprising a polynucleotide sequence which codes for the metY gene, chosen from the group consisting of a) polynucleotide which is at least 70% identical to a polynucleotide that codes for a polypeptide which comprises the amino acid sequence of SEQ ID No. 2, b) polynucleotide which codes for a polypeptide that comprises an amino acid sequence which is at least 70% identical to the amino acid sequence of SEQ ID No. 2, c) polynucleotide which is complementary to the polynucleotides of a) or b), and d) polynucleotide comprising at least 15 successive nucleotides of the polynucleotide sequence of a), b) or c), and the corresponding polypeptides having the enzymatic activity of O-acetylhomoserine sulfhydrylase.

The invention also provides the above-mentioned polynucleotides as DNA which is capable of replication, comprising:

(i) the nucleotide sequence shown in SEQ ID No. 1, or (ii) at least one sequence which corresponds to sequence (i) within the range of the degeneration of the genetic code, or (iii) at least one sequence which hybridizes with the sequence complementary to sequence (i) or (ii), and optionally (iv) sense mutations of neutral function in (i).

The invention also provides a polynucleotide comprising the nucleotide sequence as shown in SEQ ID No. 1;

a polynucleotide that codes for a polypeptide which comprises the amino acid sequence as shown in SEQ ID No. 2;

a vector containing the DNA sequence of *C. glutamicum* that codes for the metY gene, deposited in accordance with the Budapest Treaty in *Corynebacterium glutamicum* as pCREmetY on Jun. 06, 2000 under DSM 13556 and coryneform bacteria in which the metY gene is present in enhanced form, in particular by the vector pCREmetY.

The invention also provides polynucleotides which are obtained by screening a corresponding gene library of a coryneform bacterium, which comprises the complete gene or parts thereof, by means of hybridization with a probe which comprises the sequence of the polynucleotide according to the invention according to SEQ ID No.1 or a fragment thereof, and isolation of the polynucleotide sequence mentioned.

BRIEF DESCRIPTION OF THE DRAWINGS

FIG. 1 shows plasmid pCREmetY.

FIG. 2 shows plasmid pCREmetAY.

DETAILED DESCRIPTION OF THE PREFERRED EMBODIMENTS

Polynucleotides which comprise the sequences according to the invention are suitable as hybridization probes for RNA, cDNA and DNA, in order to isolate, in the full length, nucleic acids or polynucleotides or genes which code for O-acetylhomoserine sulfhydrolase or to isolate those nucleic acids or polynucleotides or genes which have a high similarity of sequence or homology with that of the O-acetylhomoserine sulfhydrolase.

Polynucleotides according to the invention are furthermore suitable as primers with which DNA of genes that code for O-acetylhomoserine sulfhydrylase can be prepared by the polymerase chain reaction (PCR).

Such oligonucleotides that serve as probes or primers comprise at least 30, preferably at least 20, very particularly at least 15 successive nucleotides. Oligonucleotides which have a length of at least 40 or 50 nucleotides are also suitable. Oligonucleotides with a length of at least 100, 150, 200, 250 or 300 nucleotides are optionally also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

The polynucleotides according to the invention include a polynucleotide according to SEQ ID No. 1 or a fragment prepared therefrom and also those which are at least 70%, preferably at least 80% and in particular at least 90% to 95% identical to the polynucleotide according to SEQ ID No. 1 or a fragment prepared therefrom.

"Polypeptides" are understood as meaning peptides or proteins which comprise two or more amino acids bonded via peptide bonds.

The polypeptides according to the invention include a polypeptide according to SEQ ID No. 2, in particular those with the biological activity of O-acetylhomoserine sulfhydrylase, and also those which are at least 70%, preferably at least 80%, and in particular which are at least 90% to 95% identical to the polypeptide according to SEQ ID No. 2 and have the activity mentioned.

The invention moreover provides a process for the fermentative preparation of amino acids, in particular L-lysine and L-methionine, using coryneform bacteria which in particular already produce amino acids, and in which at least the nucleotide sequences which code for the metY gene are enhanced, in particular over-expressed.

The term "enhancement" in this connection describes the increase in the intracellular activity of one or more enzymes in a microorganism which are coded by the corresponding DNA, for example by increasing the number of copies of the gene or genes, using a potent promoter or using a gene which codes for a corresponding enzyme having a high activity, and optionally combining these measures.

By enhancement measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on the starting microorganism.

The microorganisms which the present invention provides can prepare L-amino acids, in particular L-lysine and L-methionine, from glucose, sucrose, lactose, fructose, maltose, molasses, starch, cellulose or from glycerol and ethanol. They can be representatives of coryneform bacteria, in particular of the genus *Corynebacterium*. Of the genus *Corynebacterium*, there may be mentioned in particular the species *Corynebacterium glutamicum*, which is known among experts for its ability to produce L-amino acids.

Suitable strains of the genus *Corynebacterium*, in particular of the species *Corynebacterium glutamicum* (*C. glutamicum*), are in particular the known wild-type strains

*Corynebacterium glutamicum* ATCC13032
*Corynebacterium acetoglutamicum* TCC15806
*Corynebacterium acetoacidophilum* ATCC13870
*Corynebacterium thermoaminogenes* FERM BP-1539
*Corynebacterium melassecola* ATCC17965
*Brevibacterium flavum* ATCC14067
*Brevibacterium lactofermentum* ATCC13869 and
*Brevibacterium divaricatum* ATCC14020 or L-lysine-producing mutants or strains prepared therefrom, such as, for example

*Corynebacterium glutamicum* FERM-P 1709
*Brevibacterium flavum* FERM-P 1708
*Brevibacterium lactofermentum* FERM-P 1712

*Corynebacterium glutamicum* FERM-P 6463
*Corynebacterium glutamicum* FERM-P 6464 and
*Corynebacterium glutamicum* DSM5715.

or L-methionine-producing mutants or strains prepared therefrom, such as, for example

*Corynebacterium glutamicum* ATCC21608.

The new metY gene from *C. glutamicum* which codes for the enzyme O-acetylhomoserine sulfhydrylase (EC 4.2.99.10) has been isolated.

To isolate the metY gene or also other genes of *C. glutamicum*, a gene library of this microorganism is first set up in *Escherichia coli* (*E. coli*). The setting up of gene libraries is described in generally known textbooks and handbooks. The textbook by Winnacker: Gene und Klone, Eine Einführung in die Gentechnologie (Verlag Chemie, Weinheim, Germany, 1990), or the handbook by Sambrook et al.: Molecular Cloning, A Laboratory Manual (Cold Spring Harbor Laboratory Press, 1989) may be mentioned as an example. A well-known gene library is that of the *E. coli* K-12 strain W3110 set up in λ vectors by Kohara et al. (Cell 50, 495 –508 (1987)). Bathe et al. (Molecular and General Genetics, 252:255–265, 1996) describe a gene library of *C. glutamicum* ATCC13032, which was set up with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575).

Börmann et al. (Molecular Microbiology 6(3), 317–326)) (1992)) in turn describe a gene library of *C. glutamicum* ATCC13032 using the cosmid pHC79 (Hohn and Collins, Gene 11, 291–298 (1980)). To prepare a gene library of *C. glutamicum* in *E. coli* it is also possible to use plasmids such as pBR322 (Bolivar, Life Sciences, 25, 807–818 (1979)) or pUC9 (Vieira et al., 1982, Gene, 19:259–268). Suitable hosts are, in particular, those *E. coli* strains which are restriction- and recombination-defective. An example of these is the strain DH5αmcr, which has been described by Grant et al. (Proceedings of the National Academy of Sciences USA, 87 (1990) 4645–4649). The long DNA fragments cloned with the aid of cosmids can in turn be subcloned in the usual vectors suitable for sequencing and then sequenced, as is described e.g. by Sanger et al. (Proceedings of the National Academy of Sciences of the United States of America, 74:5463–5467, 1977).

The resulting DNA sequences can then be investigated with known algorithms or sequence analysis programs, such as that of Staden (Nucleic Acids Research 14, 217–232 (1986)), that of Marck (Nucleic Acids Research 16, 1829–1836 (1988)) or the GCG program of Butler (Methods of Biochemical Analysis 39, 74–97 (1998)).

The new DNA sequence of *C. glutamicum* which codes for the metY gene and which, as SEQ ID No. 1, is a constituent of the present invention has been found. The amino acid sequence of the corresponding protein has furthermore been derived from the present DNA sequence by the methods described above. The resulting amino acid sequence of the metY gene product is shown in SEQ ID No. 2.

Coding DNA sequences which result from SEQ ID No. 1 by the degeneracy of the genetic code are also a constituent of the invention. In the same way, DNA sequences which hybridize with SEQ ID No. 1 or parts of SEQ ID No. 1 are a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. they are of neutral function.

It is furthermore known that changes at the N and/or C terminus of a protein must not substantially impair or may even stabilize the function thereof. Information in this context can be found in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences which result in a corresponding manner from SEQ ID No. 2 are also a constituent of the invention.

In the same way, DNA sequences which hybridize with SEQ ID No. 1 or parts of SEQ ID No. 1 are a constituent of the invention. Finally, DNA sequences which are prepared by the polymerase chain reaction (PCR) using primers which result from SEQ ID No. 1 are a constituent of the invention. Such oligonucleotides typically have a length of at least 15 nucleotides.

Instructions for identifying DNA sequences by means of hybridization can be found in the handbook "The DIG System Users Guide for Filter Hybridization" from Boehringer Mannheim GmbH (Mannheim, Germany, 1993) and in Liebl et al. (International Journal of Systematic Bacteriology (1991), 41: 255–260). The hybridization takes place under stringent conditions, that is to say only hybrids are formed in which the probe and target sequence, i.e. the polynucleotides treated with the probe, are at least 70% identical. It is known that the stringency of the hybridization, including the washing steps, is influenced or determined by varying the buffer composition, the temperature and the salt concentration. The hybridization reaction is preferably carried out under a relatively low stringency compared with the washing steps (Hybaid Hybridisation Guide, Hybaid Limited, Teddington, UK, 1996).

A 5× SSC buffer at a temperature of approx. 50–68° C., for example, can be employed for the hybridization reaction. Probes can also hybridize here with polynucleotides which are less than 70% identical to the sequence of the probe. Such hybrids are less stable and are removed by washing under stringent conditions. This can be achieved, for example, by lowering the salt concentration to 2×SSC and optionally subsequently 0.5×SSC (The DIG System User's Guide for Filter Hybridisation, Boehringer Mannheim, Mannheim, Germany, 1995) a temperature of approx. 50–680° C. being established. It is optionally possible to lower the salt concentration to 0.1×SSC. Polynucleotide fragments which are, for example, at least 70% or at least 80% or at least 90% to 95% identical to the sequence of the probe employed can be isolated by increasing the hybridization temperature stepwise from 50 to 680° C. in steps of approx. 1–20° C. Further instructions on hybridization are obtainable on the market in the form of so-called kits (e.g. DIG Easy Hyb from Roche Diagnostics GmbH, Mannheim, Germany, Catalogue No. 1603558).

Instructions for amplification of DNA sequences with the aid of the polymerase chain reaction (PCR) can be found in the handbook by Gait: Oligonucleotide synthesis: A Practical Approach (IRL Press, Oxford, UK, 1984) and in Newton and Graham: PCR (Spektrum Akademischer Verlag, Heidelberg, Germany, 1994).

It has been found that coryneform bacteria produce amino acids, in particular L-lysine and L-methionine, in an improved manner after over-expression of the metY gene, optionally in combination with the metA gene.

To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative L-lysine and L-methionine production. The expression is likewise improved by measures to prolong the life of the m-RNA. Furthermore, the enzyme activity is also increased by preventing the degradation of the enzyme protein. The genes or gene constructs can either be present in plasmids with a varying number of copies, or can be integrated and amplified in the chromosome. Alternatively, an over-expression of the genes in question can furthermore be achieved by changing the composition of the media and the culture procedure.

Instructions in this context can be found in Martin et al. (Bio/Technology 5, 137–146 (1987)), in Guerrero et al. (Gene 138, 35–41 (1994)), Tsuchiya and Morinaga (Bio/Technology 6, 428–430 (1988)), in Eikmanns et al. (Gene 102, 93–98 (1991)), in European Patent Specification 0 472 869, in U.S. Pat. No. 4,601,893, in Schwarzer and Pühler (Bio/Technology 9, 84–87 (1991)), in Reinscheid et al. (Applied and Environmental Microbiology 60, 126–132 (1994)), in LaBarre et al. (Journal of Bacteriology 175, 1001–1007 (1993)), in Patent Application WO 96/15246, in Malumbres et al. (Gene 134, 15–24 (1993)), in Japanese Laid-Open Specification JP-A-10-229891, in Jensen and Hammer (Biotechnology and Bioengineering 58, 191–195 (1998)), in Makrides (Microbiological Reviews 60:512–538 (1996)) and in known textbooks of genetics and molecular biology.

By way of example, for enhancement the metY gene according to the invention was over-expressed with the aid of episomal plasmids. Suitable plasmids are those which are replicated in coryneform bacteria. Numerous known plasmid vectors, such as e.g. pZ1 (Menkel et al., Applied and Environmental Microbiology (1989) 64:549–554), pEKEx1 (Eikmanns et al., Gene 102:93–98 (1991)) or pHS2-1 (Sonnen et al., Gene 107:69–74 (1991)) are based on the cryptic plasmids pHM1519, pBL1 or pGA1. Other plasmid vectors, such as those based on pCG4 (U.S. Pat. No. 4,489,160), or pNG2 (Serwold-Davis et al., FEMS Microbiology Letters 66, 119–124 (1990)), or pAG1 (U.S. Pat. No. 5,158,891), can be used in the same manner.

Examples of such plasmid vectors are shown in FIGS. 1 and 2.

Plasmid vectors which are furthermore suitable are also those with the aid of which the process of gene amplification by integration into the chromosome can be used, as has been described, for example, by Reinscheid et al. (Applied and Environmental Microbiology 60, 126–132 (1994)) for duplication or amplification of the hom-thrB operon. In this method, the complete gene is cloned in a plasmid vector which can replicate in a host (typically *E. coli*), but not in *C. glutamicum*. Possible vectors are, for example, pSUP301 (Simon et al., Bio/Technology 1, 784–791 (1983)), pK18mob or pK19mob (Schäfer et al., Gene 145, 69–73 (1994)), PGEM-T (Promega corporation, Madison, Wis., USA), pCR2.1-TOPO (Shuman (1994). Journal of Biological Chemistry 269:32678–84; U.S. Pat. No. 5,487,993), pCR®Blunt (Invitrogen, Groningen, Holland; Bernard et al., Journal of Molecular Biology, 234:534–541 (1993)), pEM1 (Schrumpf et al, 1991, Journal of Bacteriology 173:4510–4516) or pBGS8 (Spratt et al., 1986, Gene 41:337–342). The plasmid vector which contains the gene to be amplified is then transferred into the desired strain of *C. glutamicum* by conjugation or transformation. The method of conjugation is described, for example, by Schäfer et al.

(Applied and Environmental Microbiology 60, 756–759 (1994)). Methods for transformation are described, for example, by Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross over" event, the resulting strain contains at least two copies of the gene in question.

In addition, it may be advantageous for the production of amino acids, in particular L-lysine and L-methionine, to enhance one or more enzymes of the particular biosynthesis pathway, of glycolysis, of anaplerosis, or of amino acid export, in addition to the metY gene.

Thus, for example, for the preparation of L-lysine one or more genes chosen from the group consisting of the gap gene which codes for glyceraldehyde 3-phosphate dehydrogenase (Eikmanns (1992), Journal of Bacteriology 174:6076–6086), the tpi gene which codes for triose phosphate isomerase (Eikmanns (1992), Journal of Bacteriology 174:6076–6086), the pgk gene which codes for 3-phosphoglycerate kinase (Eikmanns (1992), Journal of Bacteriology 174:6076–6086), the pyc gene which codes for pyruvate carboxylase (DE-A-198 31 609), the lysc gene which codes for a feed-back resistant aspartate kinase (ACCESSION NUMBER P26512), can be enhanced, in particular over-expressed.

Thus, for example, for the preparation of L-methionine one or more genes chosen from the group consisting of the gap gene which codes for glyceraldehyde 3-phosphate dehydrogenase (Eikmanns (1992), Journal of Bacteriology 174:6076–6086), the tpi gene which codes for triose phosphate isomerase (Eikmanns (1992), Journal of Bacteriology 174:6076–6086), the pgk gene which codes for 3-phosphoglycerate kinase (Eikmanns (1992), Journal of Bacteriology 174:6076–6086), the pyc gene which codes for pyruvate carboxylase (DE-A-198 31 609), the lysC gene which codes for a feed-back resistant aspartate kinase (ACCESSION NUMBER P26512), the metA gene which codes for homoserine O-acetyltransferase (ACCESSION Number AF052652), the metB gene which codes for cystathionine-gamma-synthase (ACCESSION Number AF126953), the aecD gene which codes for cystathionine-gamma-lyase (ACCESSION Number M89931)

the glyA gene which codes for serine hydroxymethyl-transferase (JP-A-08107788), can be enhanced, in particular over-expressed, additional enhancement of metA being particularly preferred.

It may furthermore be advantageous for the production of L-lysine, in addition to the enhancement of the metY gene, for one or more genes chosen from the group consisting of the pck gene which codes for phosphoenol pyruvate carboxykinase (DE 199 50 409.1; DSM 13047), the pgi gene which codes for glucose 6-phosphate isomerase (U.S. Ser. No. 09/396,478, DSM 12969), the poxB gene which codes for pyruvate oxidase (DE: 1995 1975.7; DSM 13114)

to be attenuated, in particular for the expression thereof to be reduced.

It may furthermore be advantageous for the production of L-methionine, in addition to the enhancement of the metY gene, for one or more genes chosen from the group consisting of the pck gene which codes for phosphoenol pyruvate carboxykinase (DE 199 50 409.1; DSM 13047), the pgi gene which codes for glucose 6-phosphate isomerase (U.S. Ser. No. 09/396,478, DSM 12969), the poxB gene which codes for pyruvate oxidase (DE: 1995 1975.7; DSM 13114)

the thrB gene which codes for homoserine kinase (ACCESSION Number P08210), the ilvA gene which codes for threonine dehydratase (ACCESSION Number Q04513), the thrC gene which codes for threonine synthase (ACCESSION Number P23669), the ddh gene which codes for meso-diaminopimelate D-dehydrogenase (ACCESSION Number Y00151), to be attenuated, in particular for the expression thereof to be reduced.

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or enzyme (protein), and optionally combining these measures.

By attenuation measures, the activity or concentration of the corresponding protein is in general reduced to 0 to 50%, 0 to 25%, 0 to 10% or 0 to 5% of the activity or concentration of the wild-type protein.

In addition to over-expression of the metY gene, optionally in combination with the metA gene it may furthermore be advantageous for the production of amino acids, in particular L-lysine and L-methionine, to eliminate undesirable side reactions, (Nakayama: "Breeding of Amino Acid Producing Micro-organisms", in: Overproduction of Microbial Products, Krumphanzl, Sikyta, Vanek (eds.), Academic Press, London, UK, 1982).

The microorganisms prepared according to the invention can be cultured continuously or discontinuously in the batch process (batch culture) or in the fed batch (feed process) or repeated fed batch process (repetitive feed process) for the purpose of production of amino acids, in particular L-lysine and L-methionine. A summary of known culture methods is described in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981).

Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substance can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus.

Organic and inorganic sulfur-containing compounds, such as, for example, sulfides, sulfites, sulfates and thiosulfates, can be used as a source of sulfur, in particular for the preparation of sulfur-containing amino acids.

The culture medium must furthermore comprise salts of metals, such as e. g. magnesium sulfate or iron sulfate, which are necessary for growth. Finally, essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH. Antifoams, such as e.g. fatty acid polyglycol esters, can be employed to control the development of foam. Suitable substances having a selective action, such as e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

The fermentation broths obtained in this way, in particular containing L-methionine, usually have a dry weight of 7.5 to 25 wt. % and contain L-methionine. It is furthermore also advantageous if the fermentation is conducted in a sugar-limited procedure at least at the end, but in particular over at least 30% of the duration of the fermentation. That is to say, the concentration of utilizable sugar in the fermentation medium is reduced to $\geq 0$ to 3 g/l during this period.

The fermentation broth prepared in this manner, in particular containing L-methionine, is then further processed. Depending on requirements all or some of the biomass can be removed from the fermentation broth by separation methods, such as centrifugation, filtration, decanting or a combination thereof, or it can be left completely in. This broth is then thickened or concentrated by known methods, such as with the aid of a rotary evaporator, thin film evaporator, falling film evaporator, by reverse osmosis, or by nanofiltration. This concentrated fermentation broth can then be worked up by methods of freeze drying, spray drying, spray granulation or by other processes to give a preferably free-flowing, finely divided powder.

This free-flowing, finely divided powder can then in turn by converted by suitable compacting or granulating processes into a coarse-grained, readily free-flowing, storable and largely dust-free product. In the granulation or compacting it is advantageous to employ conventional organic or inorganic auxiliary substances or carriers, such as starch, gelatin, cellulose derivatives or similar substances, such as are conventionally used as binders, gelling agents or thickeners in foodstuffs or feedstuffs processing, or further substances, such as, for example, silicas, silicates or stearates.

"Free-flowing" is understood as meaning powders which flow unimpeded out of the vessel with the opening of 5 mm (millimeters) of a series of glass outflow vessels with outflow openings of various sizes (Klein, Seifen, (Öle, Fette, Wachse 94, 12 (1968)).

As described here, "finely divided" means a powder with a predominant content (>50%) having a particle size of 20 to 200 μm diameter. "Coarse-grained" means products with a predominant content (>50%) having a particle size of 200 to 2000 μm diameter. In this context, "dust-free" means that the product contains only small contents (<5%) having particle sizes of less than 20 μm diameter. The particle size determination can be carried out with methods of laser diffraction spectrometry. The corresponding methods are described in the textbook on "TeilchengröBenmessung in der Laborpraxis" by R. H. Müller and R. Schuhmann, Wissenschaftliche Verlagsgesellschaft Stuttgart (1996) or in the textbook "Introduction to Particle Technology" by M. Rhodes, Verlag Wiley & Sons (1998).

"Storable" in the context of this invention means a product which can be stored for up to 120 days, preferably up to 52 weeks, particularly preferably 60 months, without a substantial loss (<5%) of methionine occurring.

Alternatively, however, the product can be absorbed on to an organic or inorganic carrier substance which is known and conventional in feedstuffs processing, for example, silicas, silicates, grits, brans, meals, starches, sugars or others, and/or mixed and stabilized with conventional thickeners or binders. Use examples and processes in this context are described in the literature (Die Mühle+Mischfuttertechnik 132 (1995) 49, page 817).

Finally, the product can be brought into a state in which it is stable to digestion by animal stomachs, in particular the stomach of ruminants, by coating processes ("coating") using film-forming agents, such as, for example, metal carbonates, silicas, silicates, alginates, stearates, starches, gums and cellulose ethers, as described in DE-C-4100920.

If the biomass is separated off during the process, further inorganic solids, for example added during the fermentation, are in general removed. In addition, the animal feedstuffs additive according to the invention comprises at least the predominant proportion of the further substances, in particular organic substances, which are formed or added and are present in solution in the fermentation broth, where these have not been separated off by suitable processes.

In one aspect of the invention, the biomass can be separated off to the extent of up to 70%, preferably up to 80%, preferably up to 90%, preferably up to 95%, and particularly preferably up to 100%. In another aspect of the invention, up to 20% of the biomass, preferably up to 15%, preferably up to 10%, preferably up to 5%, particularly preferably no biomass is separated off.

These organic substances include organic by-products which are optionally produced, in addition to the L-methionine, and optionally discharged by the microorganisms employed in the fermentation. These include L-amino acids chosen from the b group consisting of L-lysine, L-valine, L-threonine, L-alanine or L-tryptophan. They include vitamins chosen from the group consisting of vitamin BD (thiamine), vitamin B2 (riboflavin),vitamin B5 (pantothenic acid), vitamin B6 (pyridoxine), vitamin B12 (cyanocobalamin), nicotinic acid/nicotinamide and vitamin E (tocopherol). They also include organic acids which carry one to three carboxyl groups, such as, acetic acid, lactic acid, citric acid, malic acid or fumaric acid. Finally, they also include sugars, for example, trehalose. These compounds are optionally desired if they improve the nutritional value of the product.

These organic substances, including L-methionine and/or D-methionine and/or the racemic mixture D,L-methionine, can also be added, depending on requirements, as a concentrate or pure substance in solid or liquid form during a suitable process step. These organic substances mentioned can be added individually or as mixtures to the resulting or concentrated fermentation broth, or also during the drying or granulation process. It is likewise possible to add an organic substance or a mixture of several organic substances to the fermentation broth and a further organic substance or a further mixture of several organic substances during a later process step, for example granulation.

The product described above is suitable as a feedstuffs additive, i.e. feed additive, for animal nutrition.

The L-methionine content of the animal feedstuffs additive is conventionally 1 wt. % to 80 wt. %, preferably 2 wt. % to 80 wt. %, particularly preferably 4 wt. % to 80 wt. %, and very particularly preferably 8 wt. % to 80 wt. %, based on the dry weight of the animal feedstuffs additive. Contents of 1 wt. % to 60 wt. %, 2 wt. % to 60 wt. %, 4 wt. % to 60 wt. %, 6 wt. % to 60 wt. %, 1 wt. % to 40 wt. %, 2 wt. % to 40 wt. % or 4 wt. % to 40 wt. % are likewise possible. The water content of the feedstuffs additive is conventionally up to 5 wt. %, preferably up to 4 wt. %, and particularly preferably less than 2 wt. %.

The invention also provides a process for the preparation of an L-methionine-containing animal feedstuffs additive from fermentation broths, which comprises the steps a) culture and fermentation of an L-methionine-producing microorganism in a fermentation medium;

b) removal of water from the L-methionine-containing fermentation broth (concentration);

c) removal of an amount of 0 to 100 wt. % of the biomass formed during the fermentation; and d) drying of the fermentation broth obtained according to a) and/or b) to obtain the animal feedstuffs additive in the desired powder or granule form.

If desired, one or more of the following steps can furthermore be carried out in the process according to the invention:

e) addition of one or more organic substances, including L-methionine and/or D-methionine and/or the racemic mixture D,L-methionine, to the products obtained according to a), b) and/or c);

f) addition of auxiliary substances chosen from the group consisting of silicas, silicates, stearates, grits and bran to the substances obtained according to a) to d) for stabilization and to increase the storability; or g) conversion of the substances obtained according to a) to e) into a form which remains stable in an animal stomach, in particular rumen, by coating with film-forming agents.

The analysis of L-lysine and L-methionine can be carried out by ion exchange chromatography with subsequent ninhydrin derivation, as described by Spackman et al. (Analytical Chemistry, 30, (1958), 1190).

The following microorganism was deposited as a pure culture on Jun. 21, 2000 at the Deutsche Sammlung für Mikroorganismen und Zellkulturen (DSMZ=German Collection of Microorganisms and Cell Cultures, Braunschweig, Germany) in accordance with the Budapest Treaty:

*Corynebacterium glutamicum* strain DSM5715/pCREmetY as DSM 13556

The process according to the invention is used for the fermentative preparation of amino acids, in particular L-lysine and L-methionine.

The present invention is explained in more detail in the following with the aid of embodiment examples.

EXAMPLE 1

Preparation of a genomic cosmid gene library from *Corynebacterium glutamicum* ATCC 13032.

Chromosomal DNA from *Corynebacterium glutamicum* ATCC 13032 was isolated as described by Tauch et al. (1995, Plasmid 33:168–and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Diagnostics GmbH, Mannheim, Germany, Product Description SAP, Code no. 1758250). The DNA of the cosmid vector SuperCos1 (Wahl et al. (1987), Proceedings of the National Academy of Sciences, USA, 84:2160–2164), obtained from Stratagene (La Jolla, USA, Product Description SuperCos1 Cosmid Vector Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase.

The cosmid DNA was then cleaved with the restriction enzyme 15 BamHI (Amersham Pharmacia, Freiburg, Germany, Product Description BamHI, Code no. 27-0868-04). The cosmid DNA treated in this manner was mixed with the treated ATCC13032 DNA and the batch was treated with T4 DNA ligase (Amersham Pharmacia, Freiburg, Germany, Product Description T4-DNA-Ligase, Code no.27-0870-04). The ligation mixture was then packed in phages with the aid of Gigapack II XL Packing Extract (Stratagene, La Jolla, USA, Product Description Gigapack II XL Packing Extract, Code no. 200217).

For infection of the *E. coli* strain NM554 (Raleigh et al. 1988, Nucleic Acid Research 16:1563–1575) the cells were taken up in 10 mM $MgSO_4$ and mixed with an aliquot of the phage suspension. The infection and titering of the cosmid library were carried out as described by Sambrook et al. (1989, Molecular Cloning: A laboratory Manual, Cold Spring Harbor), the cells being plated out on LB agar (Lennox, 1955, Virology, 1:190) with 100 mg/l ampicillin. After incubation overnight at 37° C., recombinant individual clones were selected.

EXAMPLE 2

Isolation and Sequencing of the MetY Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Diagnostics GmbH, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany).

The DNA of the sequencing vector pZero-1, obtained from Invitrogen (Groningen, The Netherlands, Product Description Zero Background Cloning Kit, Product No. K2500-01) was cleaved with the restriction enzyme BamHI (Amersham Pharmacia, Freiburg, Germany, Product Description BamHI, Product No. 27-0868-04). The ligation of the cosmid fragments in the sequencing vector pzero-1 was carried out as described by Sambrook et al. (1989, Molecular Cloning: A Laboratory Manual, Cold Spring Harbor), the DNA mixture being incubated overnight with T4 ligase (Pharmacia Biotech, Freiburg, Germany). This ligation mixture was then electroporated (Tauch et al. 1994, FEMS Microbiol. Letters, 123:343–7) into the *E. coli* strain DH5αmcr (Grant, 1990, Proceedings of the National Academy of Sciences U.S.A., 87:4645–4649) and plated out on LB agar (Lennox, 1955, Virology, 1:190) with 50 mg/l zeocin.

reaction (PCR) and synthetic oligonucleotides. Starting from the nucleotide sequences of the methionine biosynthesis genes metY (SEQ ID No.1) and metA (gene library entry Accession Number AF052652) of *C. glutamicum* ATCC 13032, PCR primers were synthesized (MWG Biotech, Ebersberg, Germany). These primers were chosen so that the amplified fragments contain the genes and native ribosome binding sites thereof, but not possible promoter regions. In addition, suitable restriction cutting sites which allow cloning into the target vector were inserted. The sequences of the PCR primers, the cleavage sites inserted (sequence underlined) and the amplified gene (the fragment size, in bp, is listed in parentheses) are listed in the following Table 1.

TABLE 1

| Primer | Sequence with restriction cleavage site | Product | Plasmid |
| --- | --- | --- | --- |
| metY-EVP5 | 5'-CTAATAAGTCGACAAAGGAGGACA<br>SalI<br>ACCATGCCAAAGTACGAC-3' (SEQ ID NO:3) | metY<br>(1341 bp) | pCREmetY |
| metY-EVP3 | 5'-GAGTCTAATGCATGCTAGATTGCA<br>NsiI<br>GCAAAGCCG 3' (SEQ ID NO:4) | | |
| metA-EVP5 | 5'-AGAACGAATTCAAAGGAGGACAAC<br>EcoRI<br>CATGCCCACCCTCGCGC-3' (SEQ ID NO:5) | metA<br>(1161 bp) | pCREmetA |
| metA-EVP3 | 5'-GTCGTGGATCCCCTATTAGATGTA<br>PstI<br>GAACTCG-3' (SEQ ID NO:6) | | |

The plasmid preparation of the recombinant clones was carried out with Biorobot 9600 (Product No. 900200, Qiagen, Hilden, Germany). The sequencing was carried out by the dideoxy chain termination method of Sanger et al. (1977, Proceedings of the National Academy of Sciences U.S.A., 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–231) version 97-0. The individual sequences of the pZero1 derivatives were assembled to a continuous contig. The computer-assisted coding region analysis was prepared with the XNIP program (Staden, 1986, Nucleic Acids Research, 14:217–231).

The resulting nucleotide sequence is shown in SEQ ID No. 1. Analysis of the nucleotide sequence showed an open reading frame of 1313 base pairs, which was called the metY gene. The metY gene codes for a protein of 437 amino acids.

EXAMPLE 3

Construction of Aectors for Expression of MetY and MetAY 3.1. Amplification of the genes metY and metA The methionine biosynthesis genes metA and metY from *C. glutamicum* were amplified using the polymerase chain The PCR experiments were carried out with the Taq DNA polymerase from Gibco-BRL (Eggestein, Germany) in a "PCT-100 Thermocycler" (MJ Research Inc., Watertown, Mass., USA). A single denaturing step of 2 minutes at 94° C. was followed by a denaturing step of 90 seconds (sec) at 94° C., an annealing step for 90 sec at a primer-dependent temperature of T=(2×AT+4×GC) −5 C. (Suggs, et al., 1981, p. 683–693, In: D. D. Brown, and C. F. Fox (Eds.), Developmental Biology using Purified Genes. Academic Press, New York, USA) and an extension step at 72° C. lasting 90 sec. The last three steps were repeated as a cycle 35 times and the reaction was ended with a final extension step of 10 minutes (min) at 72° C. The products amplified in this way were tested electrophoretically in a 0.8% agarose gel.

The metY fragment 1341 bp in size was cleaved with the restriction endonucleases SalI and NsiI, and the metA fragment 1161 bp in size was cleaved with the restriction endonucleases EcoRI and BamHI. The two batches were separated by gel electrophoresis and the fragments metY (approx. 1330 bp) and metA (approx. 1150 bp) were isolated from the agarose gel with the QiaExII Gel Extraction Kit (Product No. 20021, Qiagen, Hilden, Germany).

3.2. Cloning of MetY in the Vector pZ8-1

The *E. coli*-*C. glutamicum* shuttle expression vector pZ8-1 (EP 0 375 889) was employed as the base vector for expression both in *C. glutamicum* and in *E. coli*. DNA of this plasmid was cleaved completely with the restriction enzymes SalI and PstI and then dephosphorylated with shrimp alkaline phosphatase (Roche Diagnostics GmbH, Mannheim, Germany, Product Description SAP, Product No. 1758250). The metY fragment isolated from the agarose gel in example 3.1 was mixed with the vector pZ8-1 prepared in this way and the batch was treated with T4 DNA ligase (Amersham Pharmacia, Freiburg, Germany, Product Description T4-DNA-Ligase, Code no.27-0870-04).

The ligation batch was transformed in the *E. coli* strain DH5α (Hanahan, In: DNA cloning. A Practical Approach. Vol. I. IRL-Press, Oxford, Washington D.C., USA). Selection of plasmid-carrying cells was made by plating out the transformation batch on LB agar (Lennox, 1955, Virology, 1:190) with 50 mg/l kanamycin. After incubation overnight at 37° C., recombinant individual clones were selected. Plasmid DNA was isolated from a transformant with the Qiaprep Spin Miniprep Kit (Product No. 27106, Qiagen, Hilden, Germany) in accordance with the manufacturer's instructions and checked by restriction cleavage. The resulting plasmid was called pCREmetY. It is shown in FIG. 1.

3.3. Cloning of MetA and MetY in the Vector pZ8-1

DNA of the plasmid pZ8-1 was cleaved completely with the restriction enzymes EcoRI and BamHI and then dephosphorylated with shrimp alkaline phosphatase (Roche Diagnostics GmbH, Mannheim, Germany, Product Description SAP, Product No. 1758250). The metA fragment isolated from the agarose gel in example 3.1 was mixed with the vector pZ8-1 prepared in this way and the batch was treated with T4 DNA ligase (Amersham Pharmacia, Freiburg, Germany, Product Description T4-DNA-Ligase, Code no.27-0870-04).

The ligation batch was transformed in the *E. coli* strain DH5α(Hanahan, In: DNA cloning. A Practical Approach. Vol. I. IRL-Press, Oxford, Washington D.C., USA). Selection of plasmid-carrying cells was made by plating out the transformation batch on LB agar (Lennox, 1955, Virology, 1:190) with 50 mg/l kanamycin. After incubation overnight at 37° C., recombinant individual clones were selected. Plasmid DNA was isolated from a transformant with the Qiaprep Spin Miniprep Kit (Product No. 27106, Qiagen, Hilden, Germany) in accordance with the manufacturer's instructions and checked by restriction cleavage. The resulting plasmid was called pCREmetA.

The plasmid pCREmetA was cleaved completely with the restriction enzymes SalI and PstI and then dephosphorylated with shrimp alkaline phosphatase (Roche Diagnostics GmbH, Mannheim, Germany, Product Description SAP, Product No. 1758250). The metY fragment isolated from the agarose gel in example 3.1 was mixed with the vector pCREmetA prepared in this way and the batch was treated with T4 DNA ligase (Amersham Pharmacia, Freiburg, Germany, Product Description T4-DNA-Ligase, Code no.27-0870-04).

The ligation batch was transformed in the *E. coli* strain DH5α (Hanahan, In: DNA cloning. A Practical Approach. Vol. I. IRL-Press, Oxford, Washington D.C., USA). Selection of plasmid-carrying cells was made by plating out the transformation batch on LB agar (Lennox, 1955, Virology, 1:190) with 50 mg/l kanamycin. After incubation overnight at 37° C., recombinant individual clones were selected. Plasmid DNA was isolated from a transformant with the Qiaprep Spin Miniprep Kit (Product No. 27106, Qiagen, Hilden, Germany) in accordance with the manufacturer's instructions and checked by restriction cleavage. The resulting plasmid was called pCREmetAY. It is shown in FIG. 2.

EXAMPLE 4

Preparation of the Strains DSM5715/pCREmetY and DSM5715/pCREmetAY

The vectors pCREmetY and pCREmetAY mentioned in example 3.2 and 3.3 were electroporated by the electroporation method of Tauch et al. (1994, FEMS Microbiological Letters, 123:343–347) in *Corynebacterium glutamicum* DSM 5715. The strain DSM 5715 is an AEC-resistant lysine producer. Selection for plasmid-carrying cells was made by plating out the electroporation batch on LB agar (Sambrook et al., Molecular Cloning: A Laboratory Manual. $2^{nd}$ Ed., Cold Spring Harbor Laboratory Press, Cold Spring Harbor, N.Y., 1989), which had been supplemented with 25 mg/l kanamycin. Plasmid DNA was isolated in each case from a transformant by conventional methods (Peters-Wendisch et al., 1998, Microbiology 144, 915–927) and checked by restriction cleavage with subsequent agarose gel electrophoresis. The strains were called DSM5715/pCREmetY and DSM5715pCREmetAY. The strain DSM5715/pCREmetY has been deposited at the Deutsche Sammlung fur Mikroorganismen und Zellkulturen (DSMZ=German Collection of Microorganisms and Cell Cultures, Braunschweig, Germany) in accordance with the Budapest Treaty as DSM 13556.

EXAMPLE 5

Preparation of Lysine with the Strain DSM5715/pCREmetY

The *C. glutamicum* strain DSM5715/pCREmetY obtained in example 4 was cultured in a nutrient medium suitable for the production of lysine and the lysine content in the culture supernatant was determined.

For this, the strain was first incubated on an agar plate with the corresponding antibiotic (brain-heart agar with kanamycin (50 mg/l)) for 24 hours at 33° C. Starting from this agar plate culture, a pre-culture was seeded (10 ml medium in a 100 ml conical flask). The complete medium CgIII was used as the medium for the pre-culture.

| Medium Cg III | |
|---|---|
| NaCl | 2.5 g/l |
| Bacto-Peptone | 10 g/l |
| Bacto-Yeast extract | 10 g/l |
| Glucose (autoclaved separately) | 2% (w/v) |
| The pH was brought to pH 7.4 | |

Kanamycin (50 mg/l) was added to this. The pre-culture was incubated for 16 hours at 33° C. at 240 rpm on a shaking machine. A main culture was seeded from this pre-culture such that the initial OD (660 nm) of the main culture was 0.1. Medium MM was used for the main culture.

| Medium MM | |
|---|---|
| CSL (corn steep liquor) | 5 g/l |
| MOPS (morpholinopropanesulfonic acid) | 20 g/l |
| Glucose (autoclaved separately) | 50 g/l |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| L-Leucine (sterile-filtered) | 0.1 g/l |
| $CaCO_3$ | 25 g/l |

The CSL, MOPS and the salt solution were brought to pH 7 with aqueous ammonia and autoclaved. The sterile substrate and vitamin solutions were then added, as well as the $CaCO_3$ autoclaved in the dry state.

Culturing is carried out in a 10 ml volume in a 100 ml conical flask with baffles. Kanamycin (50 mg/l) was added. Culturing was carried out at 33° C. and 80% atmospheric humidity.

After 48 hours, the OD was determined at a measurement wavelength of 660 nm with a Biomek 1000 (Beckmann Instruments GmbH, Munich). The amount of lysine formed was determined with an amino acid analyzer from Eppendorf-BioTronik (Hamburg, Germany) by ion exchange chromatography and post-column derivation with ninhydrin detection.

The result of the experiment is shown in Table 2.

TABLE 2

| Strain | OD(660) | Lysine HCl g/l |
|---|---|---|
| DSM5715 | 10.6 | 15.7 |
| DSM5715/pCREmetY | 9.5 | 16.1 |

EXAMPLE 6
Preparation of Methionine with the Strain DSM5715/pCREmetAY

The C. glutamicum strain DSM5715/pCREmetAY obtained in example 4 was cultured in a nutrient medium suitable for the production of methionine and the methionine content in the culture supernatant was determined.

For this, the strain was first incubated on an agar plate with the corresponding antibiotic (brain-heart agar with kanamycin (50 mg/l)) for 24 hours at 33° C. Starting from this agar plate culture, a pre-culture was seeded (10 ml medium in a 100 ml conical flask). The complete medium CgIII as described in example 5 was used as the medium for the pre-culture.

Kanamycin (50 mg/l) was added to this. The pre-culture was incubated for 16 hours at 33° C. at 240 rpm on a shaking machine. A main culture was seeded from this pre-culture such that the initial OD (660 nm) of the main culture was 0.1. The medium MM as described in example 5 was used for the main culture.

The CSL, MOPS and the salt solution were brought to pH 7 with aqueous ammonia and autoclaved. The sterile substrate and vitamin solutions were then added, as well as the CaCO₃ autoclaved in the dry state.

Culturing is carried out in a 10 ml volume in a 100 ml conical flask with baffles. Kanamycin (50 mg/l) was added. Culturing was carried out at 33° C. and 80% atmospheric humidity.

After 72 hours, the OD was determined at a measurement wavelength of 660 nm with a Biomek 1000 (Beckmann Instruments GmbH, Munich). The amount of methionine formed was determined with an amino acid analyzer from Eppendorf-BioTronik (Hamburg, Germany) by ion exchange chromatography and post-column derivation with ninhydrin detection.

The result of the experiment is shown in Table 3.

TABLE 3

| Strain | OD(660) | Methionine mg/l |
|---|---|---|
| DSM5715 | 6.6 | 1.4 |
| DSM5715/pCREmetAY | 8.3 | 16.0 |

BRIEF DESCRIPTION OF THE FIGURES

FIG. 1: Plasmid pCREmetY

FIG. 2: Plasmid pCREmetAY

The abbreviations used in the figures have the following meaning:

Kan: Resistance gene for kanamycin mety: metY gene of C. glutamicum metA: metA gene of C. glutamicum Ptac: tac promoter rrnB-T1T2: Terminator T1T2 of the rrnB gene of E. coli rep: Plasmid-coded replication origin for C. glutamicum (of pHM1519)

BamHI: Cleavage site of the restriction enzyme BamHI

EcoRI: Cleavage site of the restriction enzyme EcoRI

EcoRV: Cleavage site of the restriction enzyme EcoRV

PstI: Cleavage site of the restriction enzyme PstI

SalI: Cleavage site of the restriction enzyme SalI

XhoI: Cleavage site of the restriction enzyme XhoI

This disclosure is based on priority documents DE 100 43 334.0, DE 101 09 690.9 and U.S. Ser. No. 60/294,252, each incorporated by reference.

Obviously, numerous modifications of the invention are possible in view of the above teachings. Therefore, within the scope of the appended claims, the invention may be practiced otherwise than as specifically described herein.

What is claimed is:

1. An isolated polynucleotide which comprises SEQ ID NO:1.

2. A vector comprising the isolated polynucleotide of claim 1.

3. A host cell comprising the isolated polynucleotide of claim 1.

4. The host cell of claim 3, which is a *coryneform* bacteria.

5. The host cell of claim 3, wherein the activity of the polypeptide encoded by the isolated polynucleotide is increased relative to the host cell without the isolated polynucleotide.

6. The host cell of claim 5, wherein the activity of the polypeptide is increased at least 10% relative to the host cell without the isolated polynucleotide.

7. A process for preparing L-amino acids, comprising culturing the host cell of claim 3 for a time and under conditions suitable for the production of the L-amino acid; and isolating the L-amino acid produced.

8. The process of claim 7, wherein the L-amino acid is L-lysine and/or L-methionine.

9. The process of claim 7, wherein the host cell comprises one or more overexpressed polynucleotides which encode a protein selected from the group consisting of glycerolaldehyde 3-phosphate dehydrogenase, triose phosphate isomerase, 3-phosphoglycerate kinase, pyruvate carboxylase, aspartate kinase, cystathionine-gamma-synthase, cystathionine-gamma-lyase, and serine hydroxymethyltransferase.

10. The process of claim 7, wherein the host cell comprises one or more attenuated genes which encode proteins selected from the group consisting of phosphoenol pyruvate carboxykinase, glucose 6-phosphate isomerase, pyruvate oxidase, homoserine kinase, threonine dehydratase, threonine synthase, meso-diaminopimelate D-dehydrogenase.

11. A method of preparing an L-amino acid containing feedstuff additive, comprising (a) culturing the host cell of claim 3 in a fermentation broth for a time and under conditions suitable for the production of the L-amino acid;

(b) concentrating the L-amino acid produced;

(c) removing an amount of 0 to 100 wt % of biomass formed during the culturing; and (d) drying the fermentation broth obtained in one or both of (b) and (c) to obtain the animal feedstuff additive.

* * * * *

SEQUENCE LISTING

```
<160> NUMBER OF SEQ ID NOS: 6

<210> SEQ ID NO 1
<211> LENGTH: 1720
<212> TYPE: DNA
<213> ORGANISM: Corynebacterium glutamicum
<220> FEATURE:
<221> NAME/KEY: CDS
<222> LOCATION: (200)..(1510)

<400> SEQUENCE: 1
catcctacac catttagagt ggggctagtc ataccccat  aaccctagct  gtacgcaatc      60
gatttcaaat cagttggaaa aagtcaagaa aattacccga gaataaattt  ataccacaca     120
gtctattgca atagaccaag ctgttcagta gggtgcatgg gagaagaatt  tcctaataaa     180
aactcttaag gacctccaa atg cca aag tac gac aat tcc aat gct gac cag     232
                    Met Pro Lys Tyr Asp Asn Ser Asn Ala Asp Gln
                     1               5                   10
```

```
tgg ggc ttt gaa acc cgc tcc att cac gca ggc cag tca gta gac gca      280
Trp Gly Phe Glu Thr Arg Ser Ile His Ala Gly Gln Ser Val Asp Ala
        15                  20                  25 cag acc agc gca cga aac ctt ccg atc tac caa tcc acc gct ttc gtg      328
Gln Thr Ser Ala Arg Asn Leu Pro Ile Tyr Gln Ser Thr Ala Phe Val
        30                  35                  40 ttc gac tcc gct gag cac gcc aag cag cgt ttc gca ctt gag gat cta      376
Phe Asp Ser Ala Glu His Ala Lys Gln Arg Phe Ala Leu Glu Asp Leu
    45                  50                  55 ggc cct gtt tac tcc cgc ctc acc aac cca acc gtt gag gct ttg gaa      424
Gly Pro Val Tyr Ser Arg Leu Thr Asn Pro Thr Val Glu Ala Leu Glu
60                  65                  70                  75 aac cgc atc gct tcc ctc gaa ggt ggc gtc cac gct gta gcg ttc tcc      472
Asn Arg Ile Ala Ser Leu Glu Gly Gly Val His Ala Val Ala Phe Ser
                80                  85                  90 tcc gga cag gcc gca acc acc aac gcc att ttg aac ctg gca gga gcg      520
Ser Gly Gln Ala Ala Thr Thr Asn Ala Ile Leu Asn Leu Ala Gly Ala
            95                  100                 105 ggc gac cac atc gtc acc tcc cca cgc ctc tac ggt ggc acc gag act      568
Gly Asp His Ile Val Thr Ser Pro Arg Leu Tyr Gly Gly Thr Glu Thr
        110                 115                 120 cta ttc ctt atc act ctt aac cgc ctg ggt atc gat gtt tcc ttc gtg      616
Leu Phe Leu Ile Thr Leu Asn Arg Leu Gly Ile Asp Val Ser Phe Val
    125                 130                 135 gaa aac ccc gac gac cct gag tcc tgg cag gca gcc gtt cag cca aac      664
Glu Asn Pro Asp Asp Pro Glu Ser Trp Gln Ala Ala Val Gln Pro Asn
140                 145                 150                 155 acc aaa gca ttc ttc ggc gag act ttc gcc aac cca cag gca gac gtc      712
Thr Lys Ala Phe Phe Gly Glu Thr Phe Ala Asn Pro Gln Ala Asp Val
                160                 165                 170 ctg gat att cct gcg gtg gct gaa gtt gcg cac cgc aac agc gtt cca      760
Leu Asp Ile Pro Ala Val Ala Glu Val Ala His Arg Asn Ser Val Pro
            175                 180                 185 ctg atc atc gac aac acc atc gct acc gca gcg ctc gtg cgc ccg ctc      808
Leu Ile Ile Asp Asn Thr Ile Ala Thr Ala Ala Leu Val Arg Pro Leu
        190                 195                 200 gag ctc ggc gca gac gtt gtc gtc gct tcc ctc acc aag ttc tac acc      856
Glu Leu Gly Ala Asp Val Val Val Ala Ser Leu Thr Lys Phe Tyr Thr
    205                 210                 215 ggc aac ggc tcc gga ctg ggc ggc gtg ctt atc gac ggc gga aag ttc      904
Gly Asn Gly Ser Gly Leu Gly Gly Val Leu Ile Asp Gly Gly Lys Phe
220                 225                 230                 235 gat tgg act gtc gaa aag gat gga aag cca gta ttc ccc tac ttc gtc      952
Asp Trp Thr Val Glu Lys Asp Gly Lys Pro Val Phe Pro Tyr Phe Val
                240                 245                 250 act cca gat gct gct tac cac gga ttg aag tac gca gac ctt ggt gca     1000
Thr Pro Asp Ala Ala Tyr His Gly Leu Lys Tyr Ala Asp Leu Gly Ala
            255                 260                 265 cca gcc ttc ggc ctc aag gtt cgc gtt ggc ctt cta cgc gac acc ggc     1048
Pro Ala Phe Gly Leu Lys Val Arg Val Gly Leu Leu Arg Asp Thr Gly
        270                 275                 280 tcc acc ctc tcc gca ttc aac gca tgg gct gca gtc cag ggc atc gac     1096
Ser Thr Leu Ser Ala Phe Asn Ala Trp Ala Ala Val Gln Gly Ile Asp
    285                 290                 295 acc ctt tcc ctg cgc ctg gag cgc cac aac gaa aac gcc atc aag gtt     1144
Thr Leu Ser Leu Arg Leu Glu Arg His Asn Glu Asn Ala Ile Lys Val
300                 305                 310                 315 gca gaa ttc ctc aac aac cac gag aag gtg gaa aag gtt aac ttc gca     1192
Ala Glu Phe Leu Asn Asn His Glu Lys Val Glu Lys Val Asn Phe Ala
```

```
                     320                 325                 330
ggc ctg aag gat tcc cct tgg tac gca acc aag gaa aag ctt ggc ctg     1240
Gly Leu Lys Asp Ser Pro Trp Tyr Ala Thr Lys Glu Lys Leu Gly Leu
            335                 340                 345 aag tac acc ggc tcc gtt ctc acc ttc gag atc aag ggc ggc aag gat     1288
Lys Tyr Thr Gly Ser Val Leu Thr Phe Glu Ile Lys Gly Gly Lys Asp
        350                 355                 360 gag gct tgg gca ttt atc gac gcc ctg aag cta cac tcc aac ctt gca     1336
Glu Ala Trp Ala Phe Ile Asp Ala Leu Lys Leu His Ser Asn Leu Ala
    365                 370                 375 aac atc ggc gat gtt cgc tcc ctc gtt gtt cac cca gca acc acc acc     1384
Asn Ile Gly Asp Val Arg Ser Leu Val Val His Pro Ala Thr Thr Thr
380                 385                 390                 395 cat tca cag tcc gac gaa gct ggc ctg gca cgc gcg ggc gtt acc cag     1432
His Ser Gln Ser Asp Glu Ala Gly Leu Ala Arg Ala Gly Val Thr Gln
                400                 405                 410 tcc acc gtc cgc ctg tcc gtt ggc atc gag acc att gat gat atc atc     1480
Ser Thr Val Arg Leu Ser Val Gly Ile Glu Thr Ile Asp Asp Ile Ile
            415                 420                 425 gct gac ctc gaa ggc ggc ttt gct gca atc tagctttaaa tagactcacc       1530
Ala Asp Leu Glu Gly Gly Phe Ala Ala Ile
        430                 435 ccagtgctta aagcgctggg tttttctttt tcagactcgt gagaatgcaa actagactag    1590
acagagctgt ccatatacac tggacgaagt tttagtcttg tccacccaga acaggcggtt    1650
attttcatgc ccaccctcgc gccttcaggt caacttgaaa tccaagcgat cggtgatgtc    1710
tccaccgaag                                                           1720

<210> SEQ ID NO 2
<211> LENGTH: 437
<212> TYPE: PRT
<213> ORGANISM: Corynebacterium glutamicum

<400> SEQUENCE: 2

Met Pro Lys Tyr Asp Asn Ser Asn Ala Asp Gln Trp Gly Phe Glu Thr
1               5                   10                  15

Arg Ser Ile His Ala Gly Gln Ser Val Asp Ala Gln Thr Ser Ala Arg
            20                  25                  30

Asn Leu Pro Ile Tyr Gln Ser Thr Ala Phe Val Phe Asp Ser Ala Glu
        35                  40                  45

His Ala Lys Gln Arg Phe Ala Leu Glu Asp Leu Gly Pro Val Tyr Ser
    50                  55                  60

Arg Leu Thr Asn Pro Thr Val Glu Ala Leu Glu Asn Arg Ile Ala Ser
65                  70                  75                  80

Leu Glu Gly Gly Val His Ala Val Ala Phe Ser Ser Gly Gln Ala Ala
                85                  90                  95

Thr Thr Asn Ala Ile Leu Asn Leu Ala Gly Ala Gly Asp His Ile Val
            100                 105                 110

Thr Ser Pro Arg Leu Tyr Gly Gly Thr Glu Thr Leu Phe Leu Ile Thr
        115                 120                 125

Leu Asn Arg Leu Gly Ile Asp Val Ser Phe Val Glu Asn Pro Asp Asp
    130                 135                 140

Pro Glu Ser Trp Gln Ala Ala Val Gln Pro Asn Thr Lys Ala Phe Phe
145                 150                 155                 160

Gly Glu Thr Phe Ala Asn Pro Gln Ala Asp Val Leu Asp Ile Pro Ala
                165                 170                 175
```

-continued

Val Ala Glu Val Ala His Arg Asn Ser Val Pro Leu Ile Ile Asp Asn
            180                 185                 190

Thr Ile Ala Thr Ala Ala Leu Val Arg Pro Leu Glu Leu Gly Ala Asp
        195                 200                 205

Val Val Val Ala Ser Leu Thr Lys Phe Tyr Thr Gly Asn Gly Ser Gly
    210                 215                 220

Leu Gly Val Leu Ile Asp Gly Gly Lys Phe Asp Trp Thr Val Glu
225                 230                 235                 240

Lys Asp Gly Lys Pro Val Phe Pro Tyr Phe Val Thr Pro Asp Ala Ala
                245                 250                 255

Tyr His Gly Leu Lys Tyr Ala Asp Leu Gly Ala Pro Ala Phe Gly Leu
            260                 265                 270

Lys Val Arg Val Gly Leu Leu Arg Asp Thr Gly Ser Thr Leu Ser Ala
            275                 280                 285

Phe Asn Ala Trp Ala Ala Val Gln Gly Ile Asp Thr Leu Ser Leu Arg
        290                 295                 300

Leu Glu Arg His Asn Glu Asn Ala Ile Lys Val Ala Glu Phe Leu Asn
305                 310                 315                 320

Asn His Glu Lys Val Glu Lys Val Asn Phe Ala Gly Leu Lys Asp Ser
                325                 330                 335

Pro Trp Tyr Ala Thr Lys Glu Lys Leu Gly Leu Lys Tyr Thr Gly Ser
            340                 345                 350

Val Leu Thr Phe Glu Ile Lys Gly Gly Lys Asp Glu Ala Trp Ala Phe
        355                 360                 365

Ile Asp Ala Leu Lys Leu His Ser Asn Leu Ala Asn Ile Gly Asp Val
    370                 375                 380

Arg Ser Leu Val Val His Pro Ala Thr Thr Thr His Ser Gln Ser Asp
385                 390                 395                 400

Glu Ala Gly Leu Ala Arg Ala Gly Val Thr Gln Ser Thr Val Arg Leu
                405                 410                 415

Ser Val Gly Ile Glu Thr Ile Asp Asp Ile Ile Ala Asp Leu Glu Gly
            420                 425                 430

Gly Phe Ala Ala Ile
            435

<210> SEQ ID NO 3
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 3
ctaataagtc gacaaaggag gacaaccatg ccaaagtacg ac                    42

<210> SEQ ID NO 4
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 4
gagtctaatg catgctagat tgcagcaaag ccg                              33

<210> SEQ ID NO 5
<211> LENGTH: 41
<212> TYPE: DNA

-continued

```
<213> ORGANISM: Artificial Sequence
<220> FEATURE:
<223> OTHER INFORMATION: synthetic oligonucleotide

<400> SEQUENCE: 5
agaacgaatt caaaggagga caaccatgcc caccctcgcg c                           41

<210> SEQ ID NO 6
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 6
gtcgtggatc ccctattaga tgtagaactc g                                     31
```